United States Patent [19]
Ward et al.

[11] Patent Number: 5,475,101
[45] Date of Patent: Dec. 12, 1995

[54] DNA SEQUENCE ENCODING ENDOGLUCANASE III CELLULASE

[75] Inventors: Michael Ward, Half Moon Bay; Kathleen A. Clarkson, San Francisco; Edmund A. Larenas, San Carlos, all of Calif.; Jeffrey D. Lorch, Hudson, Wis.; Geoffrey L. Weiss, San Francisco, Calif.

[73] Assignee: Genencor International, Inc., Rochester, N.Y.

[21] Appl. No.: 32,848

[22] Filed: Mar. 17, 1993

Related U.S. Application Data

[63] Continuation-in-part of Ser. No. 862,846, Apr. 3, 1992, Pat. No. 5,328,841, which is a continuation-in-part of Ser. No. 707,647, May 30, 1991, Pat. No. 5,290,474, which is a continuation-in-part of Ser. No. 668,640, Mar. 13, 1991, abandoned, which is a continuation-in-part of Ser. No. 593,919, Oct. 5, 1990, abandoned, and a continuation-in-part of Ser. No. 678,865, Mar. 29, 1991, Pat. No. 5,246,853.

[51] Int. Cl.$^6$ .............................. C12N 9/42; C12N 15/56
[52] U.S. Cl. ...................... 536/23.74; 536/23.2; 435/209
[58] Field of Search ................................. 536/23.2, 23.7, 536/23.74; 435/209

[56] References Cited

U.S. PATENT DOCUMENTS

| | | | |
|---|---|---|---|
| 4,894,338 | 1/1990 | Knowles et al. | 435/209 |
| 4,904,599 | 2/1990 | Ozaki et al. | 435/209 |
| 5,298,405 | 3/1994 | Nevalainen et al. | 435/209 |
| 5,320,960 | 6/1994 | Bower | 435/209 |

FOREIGN PATENT DOCUMENTS

| | | |
|---|---|---|
| 8909259 | 10/1989 | WIPO . |
| 92/06184 | 4/1992 | WIPO . |
| 93/20208 | 10/1993 | WIPO . |

OTHER PUBLICATIONS

Saloheimo et al, "EGIII, a new endoglucanase from Trihodemoa . . . " *Gene* 63:11–21 (1988).
Ooi et al, "Cloning and sequence analysis of a cDNA for cellulase . . . " *Curr. Genet.* 18:217–222 (1990).
Penttilä et al, "Expression of Two *T. reesei* Endoglucanases . . . " *Yeast* 3: 175–185 (1987).
Uzcategui et al, "The 1,4–β–D–glucan glucanohydrolases . . . " *J. Biotech.* 21: 143–160 (1991).
Ward, et al., "Cloning, sequence and preliminary structural analysis of a small, high pI endoglucananse (EGIII) from *Trichoderma reesei*" The Tricel 93 Symposium, Jun. 2–5, 1993, Espoo, Finland, pp. 153–158 in *Foundation For Biotechnical And Industrial Fermentation Research*, vol. 8, edited by Suominen et al, (Nov. 1993).
Shoemaker, et al, "Cellulases: Diversity Amongst Improved *Trichoderma* Strains," *Trends in the Biology of Fermentations for Fuels and Chemicals* (A. Hollaender, R. Rabson, Rogers, Pietro, Valentine and Wolfe, eds), Plenum Publishing Corp., New York, N.Y., pp. 89–109 (1981).
Beldman, et al, "The cellulase of *Trichoderma viride*," *Eur. J. Biochem*, vol. 146, pp. 301–308 (1985).
Häkansson, et al, "Purification and Characterization of a Low Molecular Weight 1,4–β–Glucan Glucanohydrolase From the Cellulolytic Fungus *Trichoderma viride* QM 9414," *Biochimica et Biophysica Acta*, vol. 524, pp. 385–392 (1978).
Ülker, A. and Sprey, B., "Characterization of an unglycosylated low molecular weight 1,4–β–glucan–glucanohydrolase of *Trichoderma reesei*," *FEMS Microbiology Letters*, vol. 69, pp. 215–220 (1990).
Sprey, B. and Ülker, A., "Isolation and properties of a low molecular mass endoglucanase from *Trichoderma reesei*", *FEMS Microbiology Letters*, vol. 92, pp. 253–258 (1992).
Jerry Stählberg, Ph.D. Thesis, Uppsala University, Feb. 1993, pp. 16–18.

*Primary Examiner*—Stephen G. Walsh
*Attorney, Agent, or Firm*—Christopher L. Stone

[57] ABSTRACT

The present invention is directed to purified EG III cellulase enzyme isolated from *Trichoderma longibrachiatum* and the amino acid sequence of the secreted (mature) and non-secreted (preprotein) forms. The present invention is further directed to the DNA fragment and sequence that encodes the EG III cellulase enzyme. Also disclosed are methods for isolating either purified or highly enriched EG III cellulase obtained from *Trichoderma* spp. or genetically modified strains of *Trichoderma* spp.

1 Claim, 5 Drawing Sheets

| | |
|---|---|
| E. carot. EG | ASSSNDADKLYFGNNKYYLFNNVWGKDEIKGWQ-QTIFYNSPISMGW--NWHWPSSTHSVKAYPSLVSGW |
| A. aculeatus EG | QQAQLCDQYATYTGGVYTINNNLWGKDAGSGSQCTTVNSASSAGTSWSTKWNWSGGENSVKSYAN---- |
| | SYQN---- |

| | |
|---|---|
| E. carot. EG | HWTAGYTENSGLPIQLSSNKSITSNVTYSIKATGTYNAAYDIWFHTTDKANWDSSPTDELMIWLND-TNA |
| A. aculeatus EG | ---SLGTFNKKLVSQIS-QIPTTARWSYDNTGIRA-DVAYDL-FTAADINHVTWSGDYELMIWLARYGGV |
| | MPTTASWSYSGSNIRA-NVAYDL-FTAAN MIWLGKYGDI |
| | ---SQIAI TVNSISS-MPTTASW |

| | |
|---|---|
| E. carot. EG | GPAGDYIETVFLGDSSWNVFKGWINADNGGGWNVFSFVHTSGTNSASLNIRHFTDYLVQTKQWMSDEKYI |
| A. aculeatus EG | QPIGSQIATATVDGQTWEL---WYGA--NGSQKTYSFVAPTPITSFQGDVNDFFKYLTQNHGFPASSQYL |
| | NFFNYLR |
| | GPIGSSQGTVNVGGQXXXL |

| | |
|---|---|
| E. carot. EG | SSVEFGTEIF-GGDGQIDITEWRVDVK |
| A. aculeatus EG | ITLQFGTEPFTGGPATLSVSNWSASVQ |

*FIG._1*

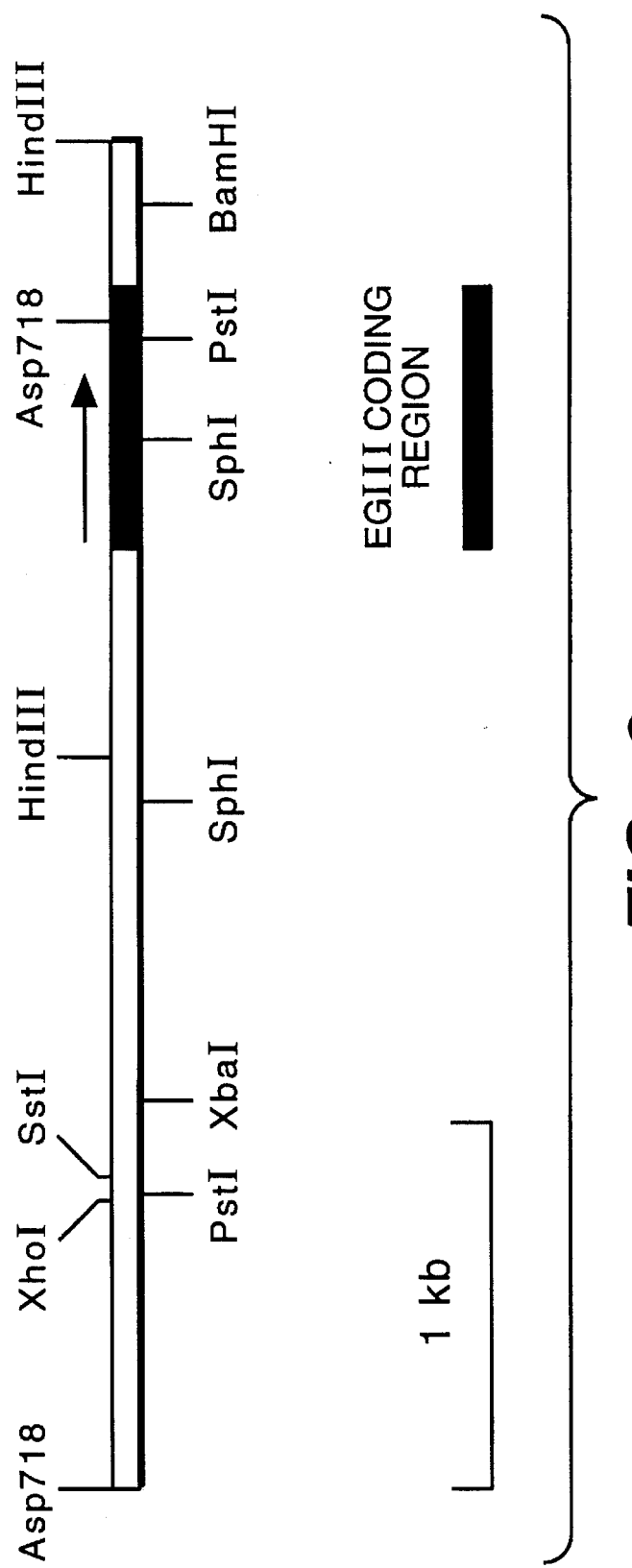
FIG._2

FIG._3

| FIG._3A |
| FIG._3B |
| FIG._3C |

FIG._3A

GGGTGGTCTGATGAAACGTCTTGGCCAAATCGTGATCGATTGATACTCGCATCTATAAGATGGCACAGA
TCGACTCTTGATTCACAGACATCCGTCAAGCCCTCAGCCTCAAGTCCAAGTCCACAAACACAAGCACAAGCA  70
TAGCGTCGCAATGAAGTTCCTTCAAGTTCCTTCAAGCTCCCTATACCGGCCCTGGCCCCAAACCAGCTGT  140
          MetLysPheLeuGlnValLeuIleProAlaLeuAlaAlaGlnThrSerCys  210
GACCAGTGGGCAACCTTCACTGGCAACGGCTACACAGTCAGCAACAACCTTTGGGAGCATCAGCCGGCT
AspGlnTrpAlaThrPheThrGlyAsnGlyTyrThrValSerAsnAsnLeuTrpGlyAlaSerAlaGly  280

```
CTGGATTTGGCTGCTGCGTGACGGCGGGTATCGCTCAGCGGGGCGGGCCTCCTGGCACGCAGACTGGCAGTGGTC                                    350
SerGlyPheGlyCysValThrAlaValSerLeuSerGlyGlyAlaSerTrpHisAlaAspTrpGlnTrpSer

CGGCGGCCAGAACAACGTCAAGTCGTACCAGAACTCTCAGATTGCCATTCCCCAGAAGAGGACCGTCAAC                                         420
GlyGlyGlnAsnAsnValLysSerTyrGlnAsnSerGlnIleAlaIleProGlnLysArgThrValAsn

AGCATCAGCAGCATGCCCACCACTGCCAGCTGGAGCTACAGCGGGAGCAACATCCCGCTAATGTTGCGT                                          490
SerIleSerSerMetProThrThrAlaSerTrpSerTyrSerGlySerAsnIleArgAlaAsnValAla

ATGACTTGTTCACCGCAGCCAACCCGAATCATGTCACGTACTCGGGAGACTACGAACTCATGATCTGgta                                         560
TyrAspLeuPheThrAlaAlaAsnProAsnHisValThrTyrSerGlyAspTyrGluLeuMetIleTrp agccataagaagtgaccctcctgatagtttcgactaacaacatgtcttgagGCTTGGCAAATACGGCGA                                           630
                                                  LeuGlyLysTyrGlyAsp
```

FIG._3B

```
TATTGGGCCGATTGGTCCTCACAGGGAACAGTCAACGTCGGTGGCCAGAGCTGGACGCTCTACTATGGC
IleGlyProIleGlySerSerGlnGlyThrValAsnValGlyGlyGlnSerTrpThrLeuTyrTyrGly                    700

TACAACGGAGCCATGCAAGTCTATTCCTTTGTGGCCCAGACCAACACTACCAACTACAGCGGAGATGTCA
TyrAsnGlyAlaMetGlnValTyrSerPheValAlaGlnThrThrAsnTyrSerGlyAspVal                          770

AGAACTTCTTCAATTATCTCCGAGACAATAAAGGATACAACGCTGCAGGCCAATATGTTCTTAgtaagtc
LysAsnPhePheAsnTyrLeuArgAspAsnLysGlyTyrAsnAlaAlaGlyGlnTyrValLeu                          840 accctcactgtgactgggctgagtttgttgcaacgtttgctaacaaaccttcgtatagGCTACCAATTT
                                                          SerTyrGlnPhe                 910

GGTACCGAGCCCTTCACGGGCAGTGGAACTCTGAACGTCGCATCCTGGACCGCATCTATCAACTAAAACC
GlyThrGluProPheThrGlySerGlyThrLeuAsnValAlaSerTrpThrAlaSerIleAsn***                       980

TGGAAACGTGAGATGTGGTGGGCATACGTTATTGAGCGAGGGAAAAAAGCATTGGATCCATTGAAGATG                   1050
```

FIG._3C

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 28 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Ile Trp Leu Gly Lys Tyr Gly Asp Ile Gly Pro Ile Gly Ser Ser Gln
1               5                   10                  15

Gly Thr Val Asn Val Gly Gly Gln Xaa Xaa Xaa Leu
            20                  25
```

( 2 ) INFORMATION FOR SEQ ID NO:2:

( i ) SEQUENCE CHARACTERISTICS:
    ( A ) LENGTH: 26 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:2:

Pro Thr Thr Ala Ser Trp Ser Tyr Ser Gly Ser Asn Ile Arg Ala Asn
1               5                   10                  15

Val Ala Tyr Asp Leu Phe Thr Ala Ala Asn
            20              25

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Thr Val Asn Ser Ile Ser Ser Met Pro Thr Thr Ala Ser Trp
    1               5                   10

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Asn Phe Phe Asn Tyr Leu Arg
    1               5

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Ser Tyr Gln Asn Ser Gln Ile Ala Ile
    1               5

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CGCGGAATTC GCNAAYGTNG CNTAYGA                                27

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

ATCTGCAGAR CCADATCATN AGYTC                    25

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

ATCTGCAGAR CCADATCATY AAYTC                    25

( 2 ) INFORMATION FOR SEQ ID NO:9:

( i ) SEQUENCE CHARACTERISTICS:
        ( A ) LENGTH: 234 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Met Lys Phe Leu Gln Val Leu Pro Ala Leu Ile Pro Ala Ala Leu Ala
 1               5                  10                  15

Gln Thr Ser Cys Asp Gln Trp Ala Thr Phe Thr Gly Asn Gly Tyr Thr
            20                  25                  30

Val Ser Asn Asn Leu Trp Gly Ala Ser Ala Gly Ser Gly Phe Gly Cys
        35                  40                  45

Val Thr Ala Val Ser Leu Ser Gly Gly Ala Ser Trp His Ala Asp Trp
    50                  55                  60

Gln Trp Ser Gly Gly Gln Asn Asn Val Lys Ser Tyr Gln Asn Ser Gln
65                  70                  75                  80

Ile Ala Ile Pro Gln Lys Arg Thr Val Asn Ser Ile Ser Ser Met Pro
                85                  90                  95

Thr Thr Ala Ser Trp Ser Tyr Ser Gly Ser Asn Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Asn Tyr Ser Gly Asp Val Lys Asn Phe Phe
            180                 185                 190
```

Asn Tyr Leu Arg Asp Asn Lys Gly Tyr Asn Ala Ala Gly Gln Tyr Val
        195                 200                 205

Leu Ser Tyr Gln Phe Gly Thr Glu Pro Phe Thr Gly Ser Gly Thr Leu
    210                 215                 220

Asn Val Ala Ser Trp Thr Ala Ser Ile Asn
225                 230

( 2 ) INFORMATION FOR SEQ ID NO:10:

( i ) SEQUENCE CHARACTERISTICS:
        ( A ) LENGTH: 218 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

Gln Thr Ser Cys Asp Gln Trp Ala Thr Phe Thr Gly Asn Gly Tyr Thr
1           5                   10                  15

Val Ser Asn Asn Leu Trp Gly Ala Ser Ala Gly Ser Gly Phe Gly Cys
            20                  25                  30

Val Thr Ala Val Ser Leu Ser Gly Gly Ala Ser Trp His Ala Asp Trp
        35                  40                  45

Gln Trp Ser Gly Gly Gln Asn Asn Val Lys Ser Tyr Gln Asn Ser Gln
    50                  55                  60

Ile Ala Ile Pro Gln Lys Arg Thr Val Asn Ser Ile Ser Ser Met Pro
65                  70                  75                  80

Thr Thr Ala Ser Trp Ser Tyr Ser Gly Ser Asn Ile Arg Ala Asn Val
                85                  90                  95

Ala Tyr Asp Leu Phe Thr Ala Ala Asn Pro Asn His Val Thr Tyr Ser
            100                 105                 110

Gly Asp Tyr Glu Leu Met Ile Trp Leu Gly Lys Tyr Gly Asp Ile Gly
        115                 120                 125

Pro Ile Gly Ser Ser Gln Gly Thr Val Asn Val Gly Gly Gln Ser Trp
130                 135                 140

Thr Leu Tyr Tyr Gly Tyr Asn Gly Ala Met Gln Val Tyr Ser Phe Val
145                 150                 155                 160

Ala Gln Thr Asn Thr Thr Asn Tyr Ser Gly Asp Val Lys Asn Phe Phe
            165                 170                 175

Asn Tyr Leu Arg Asp Asn Lys Gly Tyr Asn Ala Ala Gly Gln Tyr Val
        180                 185                 190

Leu Ser Tyr Gln Phe Gly Thr Glu Pro Phe Thr Gly Ser Gly Thr Leu
    195                 200                 205

Asn Val Ala Ser Trp Thr Ala Ser Ile Asn
210                 215

( 2 ) INFORMATION FOR SEQ ID NO:11:

( i ) SEQUENCE CHARACTERISTICS:
        ( A ) LENGTH: 1050 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
GGGTGGTCTG GATGAAACGT CTTGGCCAAA TCGTGATCGA TTGATACTCG CATCTATAAG        60
```

-continued

| | | | | |
|---|---|---|---|---|
| ATGGCACAGA | TCGACTCTTG | ATTCACAGAC | ATCCGTCAGC | CCTCAAGCCG | TTTGCAAGTC | 120 |
| CACAAACACA | AGCACAAGCA | TAGCGTCGCA | ATGAAGTTCC | TTCAAGTCCT | CCCTGCCCTC | 180 |
| ATACCGGCCG | CCCTGGCCCA | AACCAGCTGT | GACCAGTGGG | CAACCTTCAC | TGGCAACGGC | 240 |
| TACACAGTCA | GCAACAACCT | TGGGGAGCA | TCAGCCGGCT | CTGGATTTGG | CTGCGTGACG | 300 |
| GCGGTATCGC | TCAGCGGCGG | GGCCTCCTGG | CACGCAGACT | GGCAGTGGTC | CGGCGGCCAG | 360 |
| AACAACGTCA | AGTCGTACCA | GAACTCTCAG | ATTGCCATTC | CCCAGAAGAG | GACCGTCAAC | 420 |
| AGCATCAGCA | GCATGCCCAC | CACTGCCAGC | TGGAGCTACA | GCGGGAGCAA | CATCCGCGCT | 480 |
| AATGTTGCGT | ATGACTTGTT | CACCGCAGCC | AACCCGAATC | ATGTCACGTA | CTCGGGAGAC | 540 |
| TACGAACTCA | TGATCTGGTA | AGCCATAAGA | AGTGACCCTC | CTTGATAGTT | TCGACTAACA | 600 |
| ACATGTCTTG | AGGCTTGGCA | AATACGGCGA | TATTGGGCCG | ATTGGGTCCT | CACAGGGAAC | 660 |
| AGTCAACGTC | GGTGGCCAGA | GCTGGACGCT | CTACTATGGC | TACAACGGAG | CCATGCAAGT | 720 |
| CTATTCCTTT | GTGGCCCAGA | CCAACACTAC | CAACTACAGC | GGAGATGTCA | AGAACTTCTT | 780 |
| CAATTATCTC | CGAGACAATA | AAGGATACAA | CGCTGCAGGC | CAATATGTTC | TTAGTAAGTC | 840 |
| ACCCTCACTG | TGACTGGGCT | GAGTTTGTTG | CAACGTTTGC | TAACAAAACC | TTCGTATAGG | 900 |
| CTACCAATTT | GGTACCGAGC | CCTTCACGGG | CAGTGGAACT | CTGAACGTCG | CATCCTGGAC | 960 |
| CGCATCTATC | AACTAAAACC | TGGAAACGTG | AGATGTGGTG | GGCATACGTT | ATTGAGCGAG | 1020 |
| GGAAAAAAAG | CATTGGATCC | ATTGAAGATG | | | | 1050 |

( 2 ) INFORMATION FOR SEQ ID NO:12:

( i ) SEQUENCE CHARACTERISTICS:
        ( A ) LENGTH: 233 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
Ala  Ser  Ser  Ser  Asn  Asp  Ala  Asp  Lys  Leu  Tyr  Phe  Gly  Asn  Asn  Lys
 1              5                        10                       15

Tyr  Tyr  Leu  Phe  Asn  Asn  Val  Trp  Gly  Lys  Asp  Glu  Ile  Lys  Gly  Trp
               20                       25                       30

Gln  Gln  Thr  Ile  Phe  Tyr  Asn  Ser  Pro  Ile  Ser  Met  Gly  Trp  Asn  Trp
          35                       40                       45

His  Trp  Pro  Ser  Ser  Thr  His  Ser  Val  Lys  Ala  Tyr  Pro  Ser  Leu  Val
     50                       55                       60

Ser  Gly  Trp  His  Trp  Thr  Ala  Gly  Tyr  Thr  Glu  Asn  Ser  Gly  Leu  Pro
65                       70                       75                       80

Ile  Gln  Leu  Ser  Ser  Asn  Lys  Ser  Ile  Thr  Ser  Asn  Val  Thr  Tyr  Ser
                    85                       90                       95

Ile  Lys  Ala  Thr  Gly  Thr  Tyr  Asn  Ala  Ala  Tyr  Asp  Ile  Trp  Phe  His
               100                      105                      110

Thr  Thr  Asp  Lys  Ala  Asn  Trp  Asp  Ser  Ser  Pro  Thr  Asp  Glu  Leu  Met
          115                      120                      125

Ile  Trp  Leu  Asn  Asp  Thr  Asn  Ala  Gly  Pro  Ala  Gly  Asp  Tyr  Ile  Glu
     130                      135                      140

Thr  Val  Phe  Leu  Gly  Asp  Ser  Ser  Trp  Asn  Val  Phe  Lys  Gly  Trp  Ile
145                      150                      155                      160

Asn  Asn  Ala  Asp  Asn  Gly  Gly  Gly  Trp  Asn  Val  Phe  Ser  Phe  Val  His
                    165                      170                      175
```

```
        Thr  Ser  Gly  Thr  Asn  Ser  Ala  Ser  Leu  Asn  Ile  Arg  His  Phe  Thr  Asp
                       180                      185                      190

Tyr  Leu  Val  Gln  Thr  Lys  Gln  Trp  Met  Ser  Asp  Glu  Lys  Tyr  Ile  Ser
                       195                      200                      205

Ser  Val  Glu  Phe  Gly  Thr  Glu  Ile  Phe  Gly  Gly  Asp  Gly  Gln  Ile  Asp
                       210                      215                      220

Ile  Thr  Glu  Trp  Arg  Val  Asp  Val  Lys
        225                      230
```

( 2 ) INFORMATION FOR SEQ ID NO:13:

( i ) SEQUENCE CHARACTERISTICS:
         ( A ) LENGTH: 221 amino acids
         ( B ) TYPE: amino acid
         ( C ) STRANDEDNESS: single
         ( D ) TOPOLOGY: linear ( i i ) MOLECULE TYPE: protein ( x i ) SEQUENCE DESCRIPTION: SEQ ID NO:13:

```
        Gln  Gln  Ala  Gln  Leu  Cys  Asp  Gln  Tyr  Ala  Thr  Tyr  Thr  Gly  Gly  Val
        1              5                        10                       15

Tyr  Thr  Ile  Asn  Asn  Asn  Leu  Trp  Gly  Lys  Asp  Ala  Gly  Ser  Gly  Ser
                       20                       25                       30

Gln  Cys  Thr  Thr  Val  Asn  Ser  Ala  Ser  Ser  Ala  Gly  Thr  Ser  Trp  Ser
                       35                       40                       45

Thr  Lys  Trp  Asn  Trp  Ser  Gly  Gly  Glu  Asn  Ser  Val  Lys  Ser  Tyr  Ala
             50                       55                       60

Asn  Ser  Gly  Leu  Thr  Phe  Asn  Lys  Lys  Leu  Val  Ser  Gln  Ile  Ser  Gln
        65                       70                       75                       80

Ile  Pro  Thr  Thr  Ala  Arg  Trp  Ser  Tyr  Asp  Asn  Thr  Gly  Ile  Arg  Ala
                       85                       90                       95

Asp  Val  Ala  Tyr  Asp  Leu  Phe  Thr  Ala  Ala  Asp  Ile  Asn  His  Val  Thr
                       100                      105                      110

Trp  Ser  Gly  Asp  Tyr  Glu  Leu  Met  Ile  Trp  Leu  Ala  Arg  Tyr  Gly  Gly
                       115                      120                      125

Val  Gln  Pro  Ile  Gly  Ser  Gln  Ile  Ala  Thr  Ala  Thr  Val  Asp  Gly  Gln
                       130                      135                      140

Thr  Trp  Glu  Leu  Trp  Tyr  Gly  Ala  Asn  Gly  Ser  Gln  Lys  Thr  Tyr  Ser
        145                      150                      155                      160

Phe  Val  Ala  Pro  Thr  Pro  Ile  Thr  Ser  Phe  Gln  Gly  Asp  Val  Asn  Asp
                       165                      170                      175

Phe  Phe  Lys  Tyr  Leu  Thr  Gln  Asn  His  Gly  Phe  Pro  Ala  Ser  Ser  Gln
                       180                      185                      190

Tyr  Leu  Ile  Thr  Leu  Gln  Phe  Gly  Thr  Glu  Pro  Phe  Thr  Gly  Gly  Pro
                       195                      200                      205

Ala  Thr  Leu  Ser  Val  Ser  Asn  Trp  Ser  Ala  Ser  Val  Gln
                       210                      215                      220
```

( 2 ) INFORMATION FOR SEQ ID NO:14:

( i ) SEQUENCE CHARACTERISTICS:
         ( A ) LENGTH: 9 amino acids
         ( B ) TYPE: amino acid
         ( C ) STRANDEDNESS: single
         ( D ) TOPOLOGY: linear ( i i ) MOLECULE TYPE: peptide 5,475,101

23 24

-continued ( x i ) SEQUENCE DESCRIPTION: SEQ ID NO:14:

Ser Tyr Gln Asn Ser Gln Ile Ala Ile
1               5

( 2 ) INFORMATION FOR SEQ ID NO:15:

( i ) SEQUENCE CHARACTERISTICS:
( A ) LENGTH: 27 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

Met Pro Thr Thr Ala Ser Trp Ser Tyr Ser Gly Ser Asn Ile Arg Ala
1               5                   10                  15

Asn Val Ala Tyr Asp Leu Phe Thr Ala Ala Asn
            20                  25

( 2 ) INFORMATION FOR SEQ ID NO:16:

( i ) SEQUENCE CHARACTERISTICS:
( A ) LENGTH: 29 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:16:

Met Ile Trp Leu Gly Lys Tyr Gly Asp Ile Gly Pro Ile Gly Ser Ser
1               5                   10                  15

Gln Gly Thr Val Asn Val Gly Gly Gln Xaa Xaa Xaa Leu
            20                  25

( 2 ) INFORMATION FOR SEQ ID NO:17:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:17:

Asn Phe Phe Asn Tyr Leu Arg
1               5

( 2 ) INFORMATION FOR SEQ ID NO:18:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:18:

Thr Val Asn Ser Ile Ser Ser Met Pro Thr Thr Ala Ser Trp
1               5                   10

( 2 ) INFORMATION FOR SEQ ID NO:19:

( i ) SEQUENCE CHARACTERISTICS:

(A) LENGTH: 6 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:19:

Ala  Asn  Val  Ala  Tyr  Asp
     1                   5

(2) INFORMATION FOR SEQ ID NO:20:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:20:

Glu  Leu  Met  Ile  Trp  Leu
     1                   5
```

DNA SEQUENCE ENCODING ENDOGLUCANASE III CELLULASE

CROSS-REFERENCE TO RELATED APPLICATIONS

This application is a continuation-in-part of U.S. Ser. No. 07/862,846 filed Apr. 3, 1992, now U.S. Pat. No. 5,328,841, which in turn is a continuation-in-part of U.S. Ser. No. 07/707,647 filed May 30, 1991, now U.S. Pat. No. 5,290,474, which in turn is a continuation-in-part of U.S. Ser. No. 07/668,640 filed on Mar. 13, 1991, now abandoned, which in turn is a continuation-in-part of U.S. Ser. No. 07/593,919 filed Oct. 5, 1990 and now abandoned. This application is also a continuation-in-part of U.S. Ser. No. 07/678,865 filed Mar. 29, 1991 now U.S. Pat. No. 5,246,853, which in turn is a continuation-in-part of U.S. Ser. No. 07/593,919 filed Oct. 5, 1990 and now abandoned. The disclosure of the five applications are incorporated herein in their entirety by reference.

BACKGROUND OF THE INVENTION

1. Field of the Invention

The present invention is directed to purified EG III cellulase enzyme isolated from *Trichoderma longibrachiatum* and its amino acid sequence in both secreted and non-secreted forms. The present invention is further directed to a DNA sequence that encodes the EG III cellulase enzyme. The present invention further relates to methods of isolating purified and highly enriched EG III cellulase obtained from Trichoderma spp. or genetically modified strains of Trichoderma spp.

2. State of the Art

Cellulases are known in the art as enzymes that hydrolyze cellulose (β- 1,4-glucan linkages) thereby resulting in the formation of glucose, cellobiose, cellooligosaccharides, and the like. While cellulases are produced (expressed) in fungi, bacteria and the like, cellulase produced by certain fungi, and in particular by the fungal genus Trichoderma spp. (especially *Trichoderma longibrachiatum*), have been given the most attention because a complete cellulase system capable of degrading crystalline forms of cellulose is readily produced in large quantities via fermentation procedures.

In regard to the above, Wood et al, "Methods in Enzymology", 160, 25, pages 234 et seq (1988), disclose that complete fungal cellulase systems comprise several different enzyme classifications including those identified as exo-cellobiohydrolases (EC 3.2.1.91) ("CBH"), endoglucanases (EC 3.2.1.4) ("EG"), and β-glucosidases (EC 3.2.1.21) ("BG"). The fungal cellulase classifications of CBH, EG and BG can be further expanded to include multiple components within each classification. CBHs and EGs have been isolated from a variety of fungal sources.

The complete cellulase system comprising CBH, EG and BG components is required to efficiently convert crystalline cellulose to glucose. Isolated components are far less effective, if at all, in hydrolyzing crystalline cellulose. Moreover, a synergistic relationship is observed between the cellulase components, particularly if they are of different classification.

On the other hand, cellulases and components thereof, used either singularly or in combination, are also known in the art to be useful in detergent compositions, as a softening agent, and to improve the feel of cotton fabrics, and the like. However, there is a problem with using the EG I and EG II components derived from Trichoderma spp., and especially *Trichoderma longibrachiatum*, in detergent compositions. Specifically, such components have their maximal activity at acidic pHs whereas most laundry detergent compositions are formulated for use at neutral or alkaline (pH>7 to about 10) conditions. While it is disclosed in U.S. Ser. No. 07/668,640 that the use of one or more acidic endoglucanase components of *Trichoderma longibrachiatum* in detergent compositions will provide improvements in softening, color retention/restoration and feel to cotton-containing fabrics even when treated under alkaline conditions, U.S. Ser. No. 07/707,647 is directed to the discovery that the EG III component of Trichoderma spp. provides for superior and unexpected advantages in detergent compositions as compared to the EG I and EG II components of *Trichoderma longibrachiatum*.

In addition to its use in laundry detergents, EG III cellulase can be used in a pre-washing step in the appropriate solution at an intermediate pH where sufficient activity exists to provide desired improvements in color retention/restoration, softening and feel as disclosed in U.S. Ser. No. 07/707,647 filed May 30, 1991 and incorporated herein by reference.

EG III cellulase has a further use in the stonewashing process of colored fabrics wherein redeposition of a colorant onto the fabric may be reduced by employing purified EG III. This process is disclosed in U.S. Ser. No. 07/954,113 filed Sep. 30, 1992 and incorporated herein by reference.

Additionally, it is further contemplated that the high activity under neutral to alkaline conditions of EG III cellulase would be beneficial in textile processes for treating cotton-containing fabrics (see U.S. Ser. Nos. 7/677,385 and 07/678,865 which are incorporated herein by reference in their entirety) as well as in silage and/or composting processes.

Thus, it has become of increasing interest to isolate EG III in purified form or to create a Trichoderma strain which secretes a cellulase product enriched for EG III for commercial use. Others in the field have described the purification of low molecular weight endoglucanases from Trichoderma (Shoemaker et al (1981) Trends in the Biology of Fermentations for Fuels and Chemicals (Hollaender, Rabson, Rogers, Pietro, Valentine and Wolfe, Eds.), Plenum Publishing Corp., New York; Hakansson et al, (1978) Biochim. Biophys. Acta 524:385–392; Beldman et al (1985) Eur. J Biochem. 146:301–308; Ulker and Sprey (1990) FEMS Microbiol. Lett. 69:215–220 and Sprey and Ulker (1992) FEMS Microbiol. Lett. 92:253–258). However, it is not possible to determine which, if any, represent the same protein as the EG III described herein. For example, the protein isolated by Ulker and Sprey (1990) was determined to have an arginine at its amino terminus. However, the DNA sequence of the EG III encoding gene reported herein would predict that EG III has a glutamine residue at its amino terminus.

In light of the various applications of EG III, the present invention is directed to the complete characterization of EG III, i.e, the amino acid sequence and DNA sequence encoding EG III, purified from a fungal cellulase composition. The full characterization of EG III cellulase described herein will provide a cost-effective commercially available EG III cellulase product through genetic engineering and/or large scale protein purification procedures.

SUMMARY OF THE INVENTION

A single endoglucanase component called EG III derived from Trichoderma spp. has now been purified to homogeneity and the complete amino acid sequence and DNA sequence encoding this cellulase enzyme has been determined.

Accordingly, one embodiment of the present invention relates to the DNA fragment (SEQ ID NO:11) or modification thereof encoding EG III cellulase characterized in having a molecular weight of about 22 to 27 Kdaltons and endoglucanase activity. A pH optimum range of about 5.5 to 6.0 has been determined for the mature and secreted form of EG III in *Trichoderma longibrachiatum*.

In another embodiment, the present invention relates to the precursor (preprotein) and mature (secreted) forms of the EG III cellulase enzyme as shown in SEQ ID NO:9 and SEQ ID NO:10, respectively, or derivatives thereof which specify the secreted EG III protein in having a molecular weight of about 22–27 Kdaltons and endoglucanase activity.

The present invention also relates to a method for producing purified EG III cellulase enzyme from an aqueous cellulase protein mixture which can be obtained commercially or a whole cellulase composition from a wild-type Trichoderma spp. strain.

In another embodiment, the present invention relates to methods of isolating purified or highly enriched EG III by using a genetically modified Trichoderma spp. strain wherein at least one or more exo-cellobiohydrolase components, CBH I and CBH II and endoglucanase components, EG I and EG II are inactivated for the production of EG III. More particularly, the Trichoderma spp. strain is genetically modified such that CBH I, CBH II, EG I and EG II are all inactivated.

A highly enriched EG III present in the protein mixture produced from the genetically modified strains of Trichoderma spp. described above may be acquired after subjecting the mixture to a combination of filtration and ultrafiltration steps. Alternatively, the EG III present in the protein mixture produced from the above modified strains may be further purified to homogeneity using a combination of polyethylene glycol extraction and column chromatography steps.

A further embodiment of the present invention relates to a method for producing purified or highly enriched EG III cellulase enzyme from a genetically modified Trichoderma spp. strain described above that in addition overexpresses EG III. EG III protein may be overproduced in a genetically modified strain described above into which multiple copies of the EG III gene have been inserted. Highly enriched EG III or purified EG III produced from an overexpressed genetically modified strain may be obtained after subjecting the protein mixture produced from this strain to concentration and/or purification procedures described above.

BRIEF DESCRIPTION OF THE DRAWINGS

FIG. 1 shows (SEQ ID NOS:12–18)the alignment of amino acid sequences of peptides obtained from *Trichoderma longibrachiatum* EG III (SEQ ID NOS:14–18) with the sequences of the mature forms of endoglucanases from *Erwinia carotovara* var. carotovara (*E. carot.* EG SEQ. ID. NO:12) and *Aspergillus aculeatus* (*A. aculeatus* EG).

FIG. 2 is a restriction map of the cloned, overlapping HindIII and Asp718 fragments of *Trichoderma longibrachiatum* genomic DNA which include the EG III encoding gene. The direction of transcription is denoted by an arrow over the EG III coding region.

FIG. 3 shows the genomic DNA sequence of the *Trichoderma longibrachiatum* EG III encoding gene (SEQ. ID. NO.:11). The deduced amino acid sequence of EG III is shown below the DNA sequence (SEQID NOS:9 and 10). An arrow denotes the deduced signal peptidase cleavage site between the last residue of the 16 amino acid signal sequence and the first residue of the mature protein. The two introns are shown in lower case letters. Sequences which match the consensus sequences thought to be involved with splicing filamentous fungal introns are underlined (Gurr et al (1987) Gene Structure in Eukaryotic Microbes (Kinghorn, Ed.), IRL Press, Oxford, UK).

DETAILED DESCRIPTION OF THE INVENTION

The present invention relates to purified EG III cellulase protein obtained from Trichoderma and a DNA sequence encoding the protein. In another aspect, the present invention relates to a method of isolating purified or enriched EG III cellulase obtained from Trichoderma spp. or genetically modified strains of Trichoderma spp.

Within the specification certain terms are disclosed and will be defined so as to clarify the nature of the claimed invention.

The term "EG III cellulase" refers to the endoglucanase component derived from Trichoderma spp. characterized by a pH optimum of about 5.5 to 6.0, an isoelectric point (pI) of from about 7.2 to 8.0 and a molecular weight of about 22 to 27 Kdaltons. Preferably, EG III cellulase is derived from either *Trichoderma longibrachiatum* or from *Trichoderma viride*. EG III cellulase derived from *Trichoderma longibrachiatum* has a pH optimum of about 5.5 to 6.0, an estimated isoelectric point (pI) of about 7.4 and an apparent molecular weight of about 22 to 27 Kdaltons as judged by polyacrylamide gel electrophoresis. EG III cellulase derived from *Trichoderma viride* has a pH optimum of about 5.5, an isoelectric point (pI) of about 7.7 and a molecular weight of about 23.5 Kdaltons.

The pH optimum of purified EG III is determined by measuring its optimal activity in a Remazol Brilliant Blue Carboxymethylcellulose (RBB-CMC) assay. The recovered EG III after each stage of purification (described in the Examples below) is determined by EG III activity using the RBB-CMC assay. EG III activity is calculated at 40° C. using the following procedure.

5 to 10 µl of recovered EG III is added at a concentration sufficient to provide the requisite amount of enzyme in the final solution. 250 µl of 2 weight percent RBB-CMC (commercially available from MegaZyme, 6 Altona Place, North Rocks, N.S.W. 2151 Australia) is added in 0.05M citrate/phosphate buffer at a pH that may range from 4.0 to 8.0 in 0.5 pH increments. The solution is vortexed and incubated at 40° C. for 30 minutes, followed by chilling in an ice bath for 5 to 10 minutes. 1000 µl of methyl cellosolve containing 0.3M sodium acetate and 0.02M zinc acetate is added, centrifuged and the supernatant is poured into cuvettes. The optical density (OD) of the solution in each cuvette is measured at 590 nm. Higher OD levels correspond to higher levels of enzyme activity.

EG III cellulase may be purified from any strain of Trichoderma spp. which produces EG III under suitable fermentation conditions. While the particular source of EG III is not critical, preferred sources are *Trichoderma longibrachiatum* and *Trichoderma viride*. A particularly preferred source of EG III from *Trichoderma longibrachiatum* is Cytolase 123 cellulase which is commercially available from Genencor International, Inc., 180 Kimball Way, South San Francisco, Calif. 94080. Because of its high pI, EG III is found in a region of an isoelectrofocusing gel where high pI xylanases and other high pI components expressed by Trichoderma spp. are generally found. In fact, it has been hypothesized that the band identified as EG III was a degradation product of either EG I or II. However, gel isoelectrofocusing of EG I and EG II deleted cellulase (prepared in the manner of U.S. Ser. Nos. 07/593,919 and 07/668,640) demonstrated that this band was not attributable to a degradation product of either EG I or II. (See U.S. Ser. No. 07/862,846 herein incorporated by reference.)

It is noted that EG II has been previously referred to by the nomenclature "EG III" by some authors but current nomenclature uses the term "EG II". In any event, the EG II protein is substantially different from the EG III protein in its molecular weight, pI and pH optimum as evidenced by Table I of Example 2 presented below.

"Cellulase proteins" refer to cellulase proteins which contain any and all exo-cellobichydrolase (CBH) proteins, endoglucanase (EG) proteins and β-glucosidase (BG) proteins derived from wild-type fungal sources or genetically microorganism.

"Endoglucanase (EG) components" refer to the EG components of Trichoderma spp., including the EG I, EG II and EG III components of *Trichoderma longibrachiatum*.

"Exo-cellobiohydrolase (CBH) components" refer to the CBH components of Trichoderma spp. including the CBH I and CBH II components of *Trichoderma longibrachiatum*.

Several procedures suitable for obtaining purified EG III cellulase from a complete cellulase system derived from Trichoderma spp. ("whole cellulase") have previously been recited in U.S. Ser. Nos. 07/707,647, 07/678,865 and 07/862,846. The Examples described herein below disclose the complete purification of EG III cellulase to homogeneity by subjecting whole cellulase to purification procedures by repeated fractionation utilizing different fractionation columns preceded by an extraction step using polyethylene glycol 8000.

It is contemplated that essentially pure EG III cellulase can be prepared by genetically modifying microorganisms so as to produce enriched EG III cellulase that may subsequently be purified to homogeneity by following the purification procedure described herein.

Additionally, highly enriched EG III cellulase may be prepared by genetically modified microorganisms. The cell culture may then be filtered to remove the cells followed by ultrafiltration to concentrate EG III. Formulation with various salts, sugars and/or preservatives may yield a commercial product. Alternatively, highly enriched EG III cellulase may be prepared from the genetically modified microorganisms described above by an extraction step using polyethylene glycol (PEG) 8000 used to further enrich EG III. The PEG may then be removed and the concentrated EG III may be formulated with salts, sugars and/or preservatives.

For example, the cellulase protein mixture for either purified EG III or the enriched EG III component may be derived from the genetically modified Trichoderma spp. strains wherein the genes encoding the exo-cellobiohydrolases CBH I and CBH II and endoglucanases EG I and EG II have been removed. In another example, the EG III protein could be overproduced in a strain into which multiple copies of the EG III gene have been inserted. In this case, the EG III coding region may be operably linked to a different promoter such as that from the CBH I-encoding gene. Multiple copies of the EG III encoding gene may be inserted into a strain in which the genes encoding some or all of the other secreted enzymes, e.g., cellulase or xylanase, had been inactivated.

Thus, several different sources of EG III discussed above may be employed by the methods set forth in the Examples to determine the amino acid sequence of parts or all of the EG III protein using known sequencing methods.

The present invention relates to purified EG III cellulase enzyme having a molecular weight of approximately 22–27 kD, pI of approximately 7.2 to 8.0 and pH optimum in a range of about between 5.5 to 6.0, further characterized as having the amino acid sequence shown in the appended SEQ ID NO:9 (native sequence) and SEQ ID NO:10 (proposed secreted sequence) or a derivative thereof exhibiting similar biochemical characteristics as described above and having equal to or greater than 70% sequence identity with SEQ ID NO:10. Similar biochemical characteristics of the derivative of the EG III may include pH optimum that ranges from about 5.5 to about 7.0.

The term "derivative" is intended to include derivatives of the aforementioned sequences shown by the addition of one or more amino acid residues to either or both the C- and N-terminus of the native or secreted sequence, substitution of one or more amino acid residues at one or more sites in the native or secreted sequence, deletion of one or more amino acid residues at either or both ends of the native or secreted sequence, or deletions from within or insertion of one or more amino acid residues at one or more sites in the native or secreted sequence such that a sequence identity of at least 70% with SEQ ID NO:10 is retained.

The term "preprotein or native sequence" refers to the amino acid sequence of the precursor EG III prior to cleavage of the secretory signal sequence and secretion of mature EG III outside of the cell. Thus, the proprotein amino acid sequence contains a secretion signal sequence at the N-terminus. The term "secreted or mature sequence" is the amino acid sequence of EG III minus the secretory signal sequence.

The present invention also relates to a DNA sequence from the genome of *Trichoderma longibrachiatum* that comprises a DNA sequence encoding secreted EG III cellulase as described above or a precursor form of the protein. In particular, the DNA sequence of the present invention relates to SEQ ID NO:11 in the appended Sequence Listings or a modification thereof. Examples of suitable "modifications" of the DNA sequence are nucleotide substitutions, deletions or insertions which give rise to another form of EG III having the biochemical characteristics as described above. Another example of a modified DNA sequence would be isolation of complimentary DNA (cDNA) by reverse transcription of EG III mRNA by methods known in the art.

The amino acid sequence of parts of the EG III cellulase purified to homogeneity described in Example 3 below were used to design synthetic DNA probes in order to clone the gene responsible for encoding this information. The sequence of the EG III encoding gene may further be manipulated by recognized techniques and ultimately inserted into various Trichoderma spp. strains or into other microorganisms to obtain higher producing organisms for commercialization. See, for example, U.S. Ser. No. 07/593,919 filed Oct. 5, 1990 and U.S. Ser. No. 07/668,640 filed Mar. 13, 1991, both of which disclose methods for genetically engineering *Trichoderma longibrachiatum* so that the modified microorganism is incapable of expressing one or more of the cellulase genes and, in fact, may overproduce another cellulase. The disclosures of both U.S. Ser. No. 07/593,919 filed Oct. 5, 1990 and U.S. Ser. No. 07/668,640 filed Mar. 13, 1991 are incorporated herein by reference in their entirety.

It has been shown that specific genes within the *Trichoderma longibrachiatum* genome can be inactivated by deletion of part or all of the gene or insertion of other DNA sequences into the gene. It is, for example, possible to create strains in which some or all of the genes encoding the major cellulases (CBH I, CBH II, EG I, or EG II) have been inactivated. As a result the culture supernatant obtained from these strains would not contain these major cellulase enzymes. In turn this would simplify purification of EG III as has previously been suggested in U.S. Ser. No. 07/862,846 incorporated herein by reference.

Overproduction of EG III by *Trichoderma longibrachiatum* could be achieved by inserting multiple copies of the EG III encoding gene into the genome of this fungus (exemplified previously for EG I described in U.S. Ser. No. 07/954,113 incorporated by reference in its entirety). In order to maximize production of EG III it may be desirable to operably link the EG III coding region to a highly efficient promoter region obtained from another gene such as that encoding CBH I.

Additionally, one may wish to utilize a strain of *Trichoderma longibrachiatum* in which the genes encoding the major cellulases had been inactivated as a host for overproduction of EG III. Secretion of EG III would be attained by using the coding region of EG III native preprotein having its own secretion signal. However, secretion of mature EG III may also be possible if a different signal sequence was employed or if EG III was produced as a fusion protein attached to another secreted protein. For example, the signal sequence of CBH I could be fused with the coding region for mature EG III to allow efficient secretion of EG III. The coding region for EG III may, for example, be fused to the coding region for another cellulase (e.g., CBH I) or parts thereof, or for another secreted enzyme (e.g., protease or amylase) or parts thereof, so that a secreted fusion protein is produced.

Additionally, it would be possible to express the EG III encoding gene other microorganisms, including, but not limited to, yeast species such as *Saccharomyces cerevisiae, Pichia pastoris, Hansenula polymorpha, Kluyveromyces lactis, Yarrowia lipolytica, Schanniomyces occidentalis*, etc. See, for example, PCT application Publication No. WO 85/04672. In order to obtain expression in the alternative, non-Trichoderma hosts, it may be necessary to functionally combine the EG III coding DNA sequence (after first removing the introns of the EG III encoding gene) with promoter and terminator sequences obtained from a gene from that particular host. It may also be necessary to substitute the DNA sequence encoding a secretion signal sequence from the alternative host for the DNA sequence encoding the EG III secretion signal sequence. Production and secretion of EG III in other organisms could enable EG III to be obtained in substantially pure form.

The cloned EG III encoding DNA could be used as a molecular probe in experiments designed to clone similar genes from other filamentous fungi. In this way it may be possible to clone genes encoding EG III-like enzymes from organisms including, but not restricted to, species of Trichoderma, Humicola, Aspergillus, Neurospora, Acremonium (Chrysosporium), Penicillium, Phanaerochaete or Trametes. "EG III-like" is defined herein as to describe an enzyme derived from the above genera characterized as having a pH optimum of about between 5.5 and 7.0 based on the RBB-CMC assay and having at least 50% identity to the amino acid sequence shown in ID SEQ NO:10.

The following examples are offered to illustrate the present invention and should not be construed in any way as limiting the scope of this invention.

EXAMPLES

Example 1 demonstrates the isolation of EG III from Cytolase 123 cellulase (a complete fungal cellulase composition obtained from *Trichoderma longibrachiatum* and available from Genencor International, Inc., South San Francisco, Calif.) via purification procedures. A complete fungal cellulase composition containing EG III is also available commercially from other sources including those sold under the trade name of Rapidase RL™ (from Gistbrocades, Netherlands).

Additionally, complete fungal cellulase compositions may be found in fermentation cultures of *Trichoderma longibrachiatum* strains which are commercially available and on deposit at the American Type Culture Collection.

In order to enhance the efficiency of the isolation of EG III, it may be desirable to employ *Trichoderma longibrachiatum* genetically modified so as to overexpress EG III and/or to be incapable of producing one or more of EG I, EG II, CBH I and/or CBH II components. This will necessarily lead to more efficient isolation of EG III by, for example, PEG extraction as described below. Production of some of these strains of *Trichoderma longibrachiatum* are disclosed in U.S. Ser. No. 07/668,640 filed Mar. 13, 1991.

Example 1

Large Scale Extraction of EG III Cellulase Enzyme

One hundred liters of cell free cellulase filtrate were heated to about 30° C. The heated material was made about 4% wt/vol PEG 8000 (polyethylene glycol, MW of about 8000) and about 10% wt/vol anhydrous sodium sulfate. The mixture formed a two phase liquid mixture. The phases were separated using an SA-1 disk stack centrifuge. The phases were analyzed using silver staining isoelectric focusing gels. Fractionation and enrichment were obtained for EG III and xylanase. The recovered composition contained about 20 to 50 weight percent of EG III.

Regarding the above procedure, use of a polyethylene glycol having a molecular weight substantially less than about 8000 gave inadequate separation; whereas, use of polyethylene glycol having a molecular weight substantially greater than about 8000 resulted in the exclusion of desired enzymes in the recovered composition. With regard to the amount of sodium sulfate, sodium sulfate levels substantially greater than about 10% wt/vol caused precipitation problems; whereas, sodium sulfate levels substantially less than about 10% wt/vol gave poor separation or the solution remained in a single phase.

The enriched EG III solution from the PEG extraction was diafiltered using an omega series tangential flow 8,000 ultra filtration membrane (Filtron Technology Corp., Northborough, Mass.) against 10 mM, pH 4.0 citrate/phosphate buffer. The solution was loaded onto an equilibrated (pH 4.0, 10 mM citrate/phosphate) SP Trisacryl column. The EG III component was eluted with 250 mM sodium chloride.

Example 2

Purification of EG III to Homogeneity Via Fractionation

In order to isolate EG III to a level of homogeneity to perform amino acid sequence analysis, the EG III composition described in Example 1 was further subjected to column chromatography. The further fractionation was done on a FPLC system using a Mono-S-HR 5/5 column (available from Pharmacia LKB Biotechnology, Piscataway, N.J.). The FPLC system consists of a liquid chromatography controller, 2 pumps, a dual path monitor, a fraction collector and a chart recorder (all of which are available from Pharmacia LKB Biotechnology, Piscataway, N.J.). The fractionation was conducted by desalting 5 ml of the EG III sample prepared in Example 1 with a 20 ml Sephadex G-25 column which had been previously equilibrated with 10 mM sodium citrate pH 4. The solution was loaded onto mono-S-HR 5/5 column previously equilibrated with 10 mM sodium citrate pH 4.0 and eluted with 0–200 mM aqueous gradient of NaCl at 1%/min with a flow rats of 0.5 ml/minute with samples collected in 1 ml fractions. EG III was recovered in two fractions and was determined to be greater than 90% pure by SDS gel electrophoresis.

EG III purified in the above manner has the following characteristics which are compared to the other endoglucanases isolated from *Trichoderma longibrachiatum*.

TABLE I

|        | MW        | pI[1] | pH optimum[2] |
|--------|-----------|-------|---------------|
| EG I   | ~47–49 kD | 4.7   | ~5            |
| EG II  | ~35 kD    | 5.5   | ~5            |
| EG III | ~22–27 kD | 7.4   | ~5.5–6.0      |

[1]pI value is an estimate based on isoelectrofocusing gels.
[2]pH optimum determined by RBB-CMC activity.

As can be seen from the above table, EG III has beth a higher pH optimum and a higher pI as compared to the other endoglucanase components of *Trichoderma longibrachiatum*. It has also been shown that EG III retains significant RBB-CMC activity under alkaline pHs (disclosed in U.S. Ser. No. 07/862,846).

Likewise, EG III cellulase from other strains of Trichoderma spp. can be purified in the same manner as described above. For example, EG III cellulase derived from *Trichoderma viride* has been described by Voragen et al, Methods in Enzymology, 160:243–249. This reference describes the EG III cellulase as having a molecular weight of about 23.5 Kdaltons, a pH optimum of 5.5, and a pI of 7.7.

Example 3

Amino Acid Sequence Determination of EG III

Purified EG III was cleaved to produce smaller peptides by treatment with either cyanogen bromide or trypsin as follows. First, the EG III was precipitated by adding 900 microliters of acetone to 100 microliters of 1 mg/ml solution of EG III. After incubation at −20° C. for 10 minutes the precipitated EG III was collected by centrifugation and the pellet was dried. For cyanogen bromide treatment the EG III pellet was dissolved in 100 microliters of 6M urea in 88% formic acid; 10 microliters of 200 mg/ml solution of cyanogen bromide was added and the mixture incubated for 4 hours at 25° C. For trypsin treatment the EG III pellet was dissolved in 50 microliters of Tris (pH 8.0), 2M urea, 0.5% trifluoroacetic acid (TFA); 5 micrograms of trypsin was added and the mixture incubated at 37° C. for 4 hours.

The resulting peptides were individually purified by high pressure liquid chromatography (HPLC) as follows. A Synchropak RP-4 column was equilibrated in deionized water with 0.5% triethylamine (TEA) and 0.5% trifluoroacetic acid. The sample was loaded and then eluted with a gradient of 99% acetonitrile, 0.5% TEA, 0.5% TFA at 1% per minute.

The amino acid sequences of the amino-terminal regions of the peptides were determined by the method of Edman using a fully automated apparatus (Edman, P. and Begg, G. (1967) Eur. J. Biochem. 1:80–91). The sequences obtained are shown below. Since cyanogen bromide is known to cleave proteins after methionine residues both peptide 1 and peptide 2 shown below would be expected to be preceded by methionine in the intact protein.

Peptide 1 (SEQ ID NO:1) obtained by cyanogen bromide cleavage:
IWLGKYGDGPIGSSQGTVNVGGQXXXL
Peptide 2 (SEQ ID NO:2) obtained by cyanogen bromide cleavage: PTTASWSYSGSNIRANVAYDLFTAAN
Peptide 3 (SEQ ID NO:3) obtained by trypsin cleavage: TVNSISSMPTTASW
Peptide 4 (SEQ ID NO:4) obtained by trypsin cleavage: NFFNYLR
Peptide 5 (SEQ ID NO:5) obtained by trypsin cleavage: SYQNSQIAI The peptide sequences shown above were compared to the known amino acid sequence of endoglucanases from *Aspergillus aculeatus* (Ooi et al (1990) Curr. Genet. 18:217–222; Ooi et al (1990) Nucl. Acids Res. 8:5884) and *Erwina carotovara* subsp. *carotovara* (Saarilahti et al, Gene 90:9–14) and similarities were observed (FIG. 1).

Example 4

Cloning the Gene Encoding EG III

Three degenerate pools of oligonucleotides were synthesized according to the sequences given below. One of these pools (1) was designed to include an EcoRI restriction site at the 5' end and to contain all possible DNA sequences which could encode the amino acid sequence ANVAYD (SEQ ID NO:19), with only the first two nucleotides of the aspartate codon being used. The other two pools were designed to have a PstI restriction site at the 5' end and between them to contain the reverse complement of all possible DNA sequences encoding the amino acid sequence ELMIWL (SEQ ID NO:20), with only the first two nucleotides of the terminal leucine codon being used.

Pool 1 (256 different 27mers) (SEQ ID NO:6)
CGCGGAATTCGC(N)AA(C/T)GT(N)GC(N)TA(C/T)GA
Pool 2 (48 different 25mers) (SEQ ID NO:7)
ATCTGCAGA(A/G)CCA(A/G/T)ATCAT(N)AG(T/C)TC
Pool 3 (24 different 25mers) (SEQ ID NO:8)
ATCTGCAGA(A/G)CCA(A/G/T)ATCAT(C/T)AA(T/C)TC It was postulated that these primers could be used in pairs (either 1 with 2, or 1 with 3) in order to amplify an approximately 100 bp *T. longibrachiatum* DNA fragment using a polymerase chain reaction (PCR) procedure.

Complementary DNA (cDNA) was prepared using a commercial kit (Invitrogen Corp., San Diego, Calif.) from poly(A) RNA extracted from a culture of *T. longibrachiatum* induced for cellulase production by growth with crystalline cellulose as the sole carbon source. PCR was performed with this DNA as a template and using the oligonucleotides described above as primers. The best combination of oligonucleotides appeared to be Pool 1 used in combination with Pool 2 in that the highest abundance of a 100 bp DNA fragment was amplified using these as primers. This 100 bp DNA fragment was gel purified, digested with EcoRI and PstI, and ligated with M13mp19 DNA which had also been cut with EcoRI and PstI. Following transfection into E. coli single-stranded DNA was isolated from individual M13 plaques for DNA sequence analysis. Clones were identified which contained a 100 bp DNA fragment, the sequence of which suggested that it encoded the expected portion of EG III protein.

Total DNA was extracted from *T. longibrachiatum* strain RL-P37 and digested with various restriction enzymes. The digested DNA was subjected to agarose gel electrophoresis, transferred to a nylon membrane and hybridized with radiolabelled DNA from an M13 clone containing the 100 bp PCR fragment. From this Southern analysis it was determined that the EG III coding region resided on a 3 kb Asp718 fragment of genomic DNA. A gene library was constructed by size fractionating (around 3 kb) Asp718 digested RL-P37 genomic DNA and ligating this with Asp718 digested pUC219. Plasmid pUC219 is derived from pUC119 (described by Wilson et al (1989) Gene 77:69–78) by expanding the multiple cloning sits to include restriction sites for BglII, ClaI and XhoI.

Following transformation of the ligated DNA into *E. coli* cells and selection for ampicillin resistance the resulting colonies were screened by colony hybridization using the 100 bp PCR fragment as a probe. DNA was isolated from the positive colonies and a restriction map was generated (see FIG. 2). It was noted that the 100 bp PCR fragment of EG III hybridized very near to one end of the cloned 3 kb Asp718 fragment containing the EG III encoding gene. As a result it was necessary to clone an overlapping HindIII fragment of RL-P37 genomic DNA in order to obtain the entire gene for EG III.

The DNA sequence of the EG III coding region and some of the flanking DNA was determined and is shown in FIG. 3. Based on similarity between this DNA sequence and that of the *A. aculeatus* endoglucanase gene disclosed by Ooi et al, Applicants were able to distinguish the start and end of the coding region and to identify two introns which interrupt the coding region. These introns contain sequences at their 5' and 3' ends as well as an internal 6 bp sequence which match the consensus sequences considered to be important for splicing fungal introns. Applicants deduce that EG III is initially synthesized as a preprotein having a 16 amino acid secretion signal sequence at the amino-terminus. If this is the case, the final three amino acids of the signal sequence would be Ala Leu Ala, which is in agreement with the consensus cleavage sits for signal peptidase which serves to remove the signal sequence during protein secretion, see Perlman, D. and Halvorson, H. O. (1983) J. Mol. Biol. 167:391–409. Cleavage by signal peptidase to remove the signal sequence would yield a protein of 219 amino acids with the amino-terminal residue being Gln. In contrast, the low molecular weight endoglucanase purified by Ulker and Sprey ((1990 ) FENS Microbiol. Lett. 69:215–220) was thought to have Arg as the amino terminal residue and to have approximately 235 amino acids. The endoglucanase purified by Hakansson et al was judged to contain 197 amino acid residues.

While the foregoing invention has been described in some detail for the purposes of clarity and understanding, it will be appreciated by one skilled in the art from a reading of this disclosure that various changes in form and detail can be made without departing from the true scope of the invention and appended claims.

What is claimed is:

1. An isolated DNA sequence encoding endoglucanase III consisting of the DNA sequence shown in SEQ ID NO:11, or a modification thereof wherein the encoded endoglucanase III has a molecular weight of about 22–27 kD and a pI of about 7.2–8.0.

* * * * *